United States Patent [19]
Metz

[11] Patent Number: 5,981,260
[45] Date of Patent: Nov. 9, 1999

[54] PROCESS FOR THE PRODUCTION OF CELL MASS AND/OR FERMENTATION PRODUCTS UNDER STERILE CONDITIONS

[76] Inventor: Michael Metz, Alte Weinsteige 18, D-7000 Stuttgart 1, Germany

[21] Appl. No.: 07/795,899

[22] Filed: Nov. 21, 1991

[30] Foreign Application Priority Data

Nov. 23, 1990 [DE] Germany ............... 40 37 325

[51] Int. Cl.⁶ ............... C12P 7/06; C12N 1/00
[52] U.S. Cl. ............ 435/243; 435/161; 435/162; 435/813
[58] Field of Search ............... 435/243, 162, 435/161, 813

[56] References Cited

U.S. PATENT DOCUMENTS

| | | | |
|---|---|---|---|
| 3,591,455 | 7/1971 | Oppermann | 195/28 |
| 3,751,263 | 8/1973 | Hall | 99/31 |
| 3,857,757 | 12/1974 | Herrick et al. | 195/109 |
| 3,956,482 | 5/1976 | Hahn et al. | 424/93 |
| 4,042,460 | 8/1977 | Diers | 195/65 |
| 4,105,804 | 8/1978 | Terui et al. | 426/656 |
| 4,155,813 | 5/1979 | Barker et al. | 195/49 |
| 4,156,630 | 5/1979 | Muller | 195/115 |
| 4,167,450 | 9/1979 | Chesbro et al. | 435/3 |
| 4,342,835 | 8/1982 | Hitzman et al. | 435/255 |
| 4,357,424 | 11/1982 | Bu'Lock | 435/162 |
| 4,399,223 | 8/1983 | Vanderveen et al. | 435/261 |
| 4,865,969 | 9/1989 | Amen et al. | 435/3 |
| 4,885,241 | 12/1989 | Millichip | 435/42 |
| 4,985,355 | 1/1991 | Millichip | 435/42 |

FOREIGN PATENT DOCUMENTS

| | | |
|---|---|---|
| 0051151 | 10/1981 | European Pat. Off. . |
| 0055382 | 10/1981 | European Pat. Off. . |
| 0046344 | 3/1982 | European Pat. Off. . |
| 0065895 | 4/1982 | European Pat. Off. . |
| 0156176 | 2/1985 | European Pat. Off. . |
| 0315944 | 5/1989 | European Pat. Off. . |
| 2021600 | 7/1970 | France . |
| 2259903 | 8/1975 | France . |
| 2611742 | 9/1988 | France . |
| 1024514 | 7/1981 | U.S.S.R. . |

OTHER PUBLICATIONS

Chemical Abstracts, Vo. 77, 1972, Ref. 112482e.

*Primary Examiner*—David M. Nafe
*Assistant Examiner*—Deborah K. Ware
*Attorney, Agent, or Firm*—Webb Ziesenheim Bruening Logsdon Orkin & Hanson, P.C.

[57] ABSTRACT

Process for the production of cell mass and/or fermentation products under sterile conditions, during which the fermentation mixture, at least at times, is recycled and the metabolic products of the cultivated cells, and possibly the cell mass are separated; the process comprises the following steps:

charging the fermentation equipment with a sufficient amount of nutrient medium to start the required cell culture.

sterilizing the equipment as well as adjustment of the required concentration of nutrient medium, inoculation of the nutrient medium with the starter culture and allowing undisturbed growth of the culture for a defined time, increasing the concentration of the nutrient medium to the specific nutrient medium concentration of the cell culture by simultaneously increasing the volume of the nutrient medium to the working volume of the fermenter and increasing the concentration of cells, transition to continuous procedure with exchange of the nutrient medium and separation of the metabolic products as well as complete or partial cell recycling, termination of the continuous procedure at a required time, harvest of the cell mass under sterile conditions, and possibly repetition of some or all of the abovementioned steps in the order stated, as well as a device for the implementation of these processes.

12 Claims, 11 Drawing Sheets

FIG. 2

| Fermenter Volume (l)<br>Type of Medium | 4300<br>Culture Medium | 1000<br>Medium Concentrate |
|---|---|---|
| Time to heat to 121°C (min) | 80 | 45 |
| Sterilization time (min) | 30 | 30 |
| Time to cool to 30°C (min) | 95 | 80 |
| Total Time (min) | 205 | 155 |
| Share of Time (%) | 100 | 75,6 |
| Requirement for Town Gas ($m^3$) | 146,9 | 40 |
| Share of town gas (%) | 100 | 27,2 |
| Requirement for Cooling Water ($m^3$) | 28 | 7 |
| Share of Cooling water (%) | 100 | 25 |
| Current Requirement (Usage Units) | 37 | 10 |
| Current Share (%) | 100 | 27 |

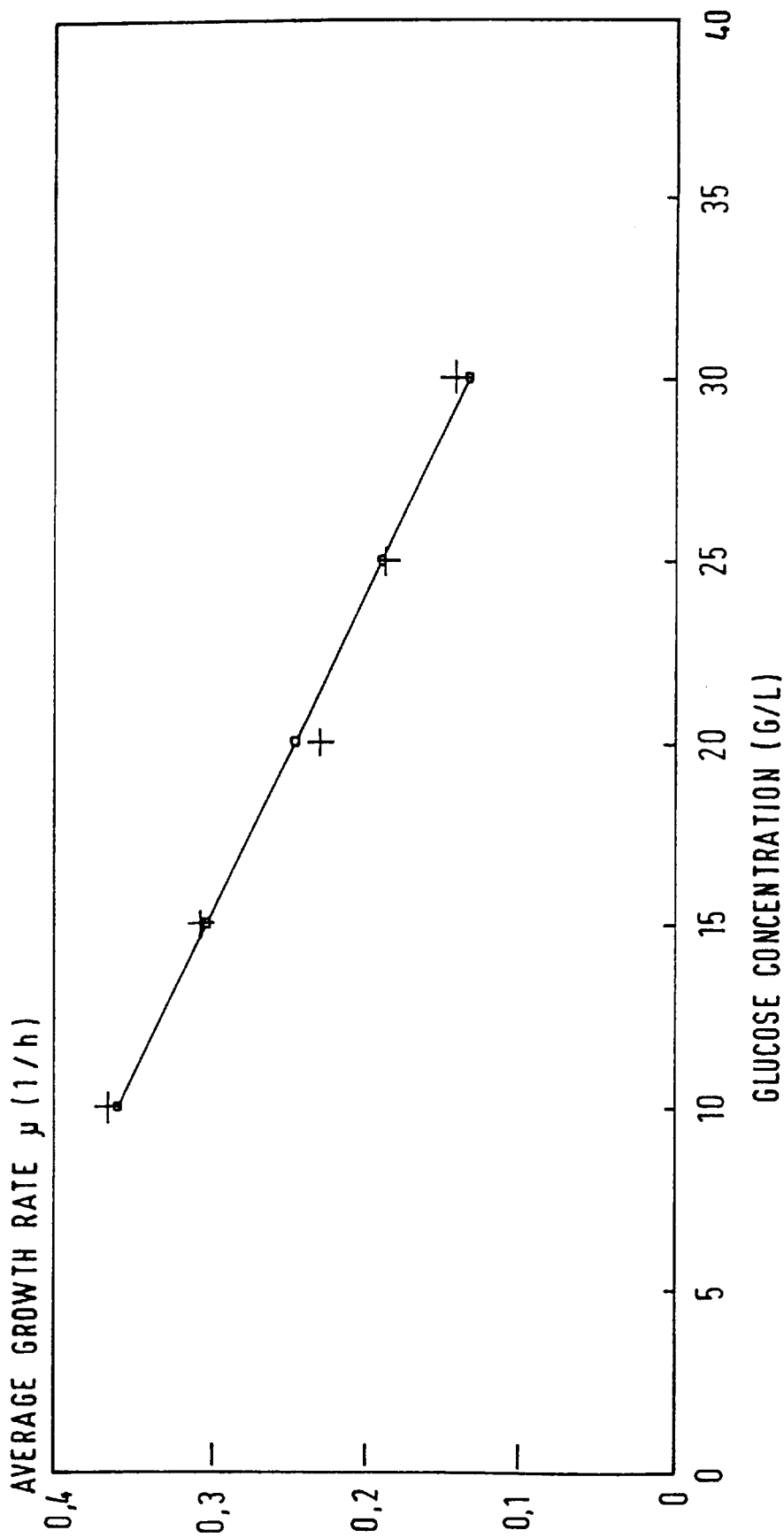

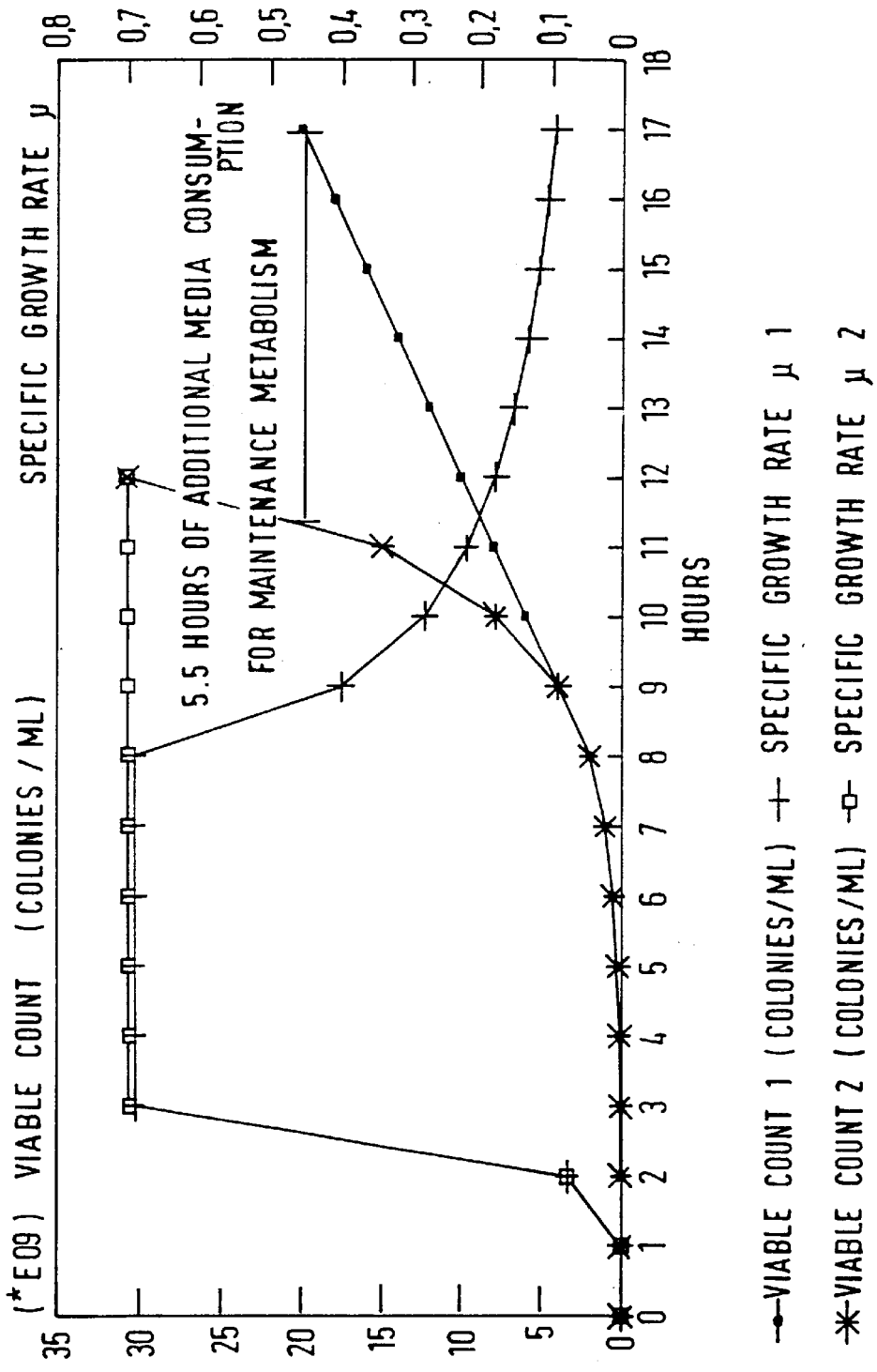

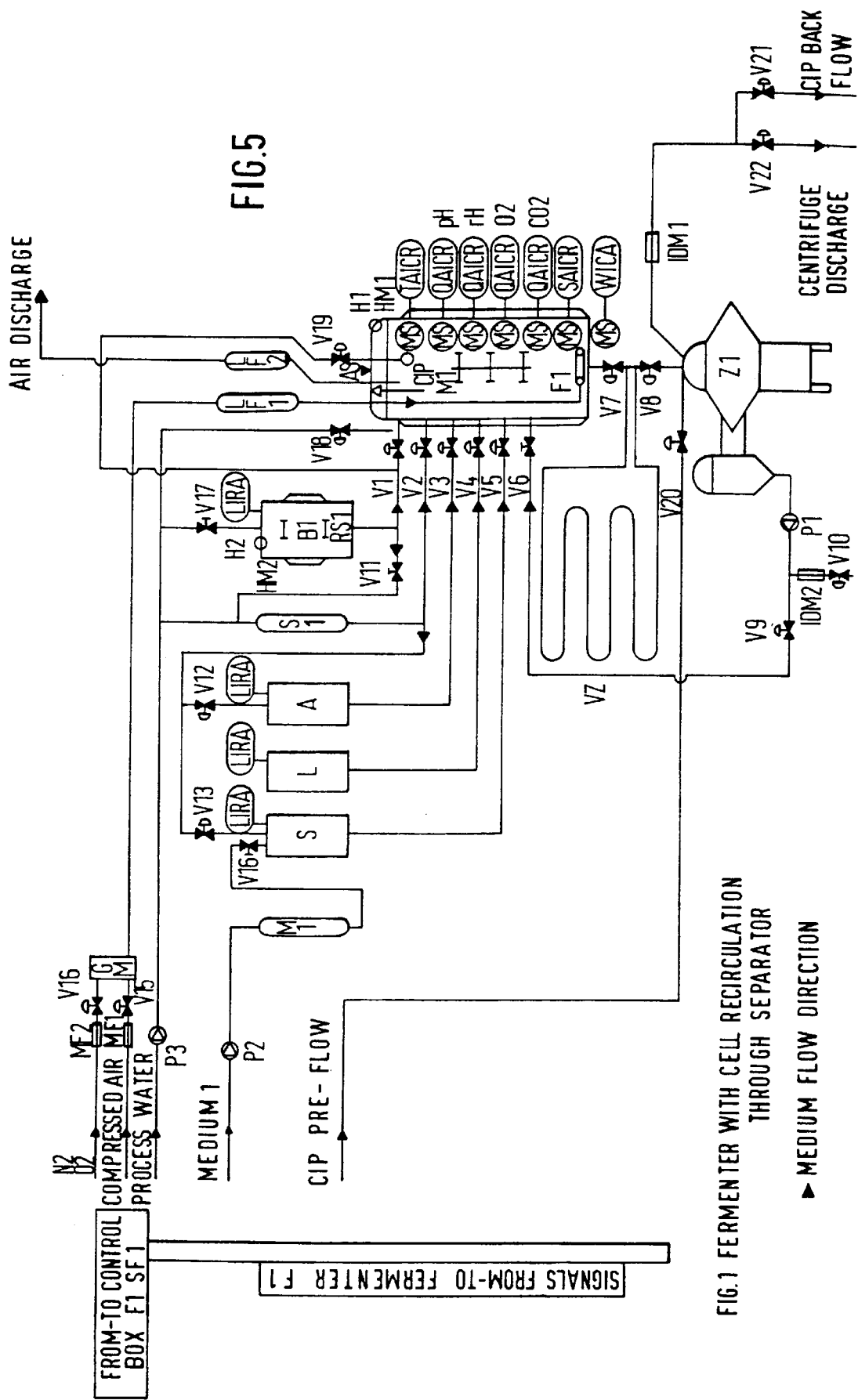

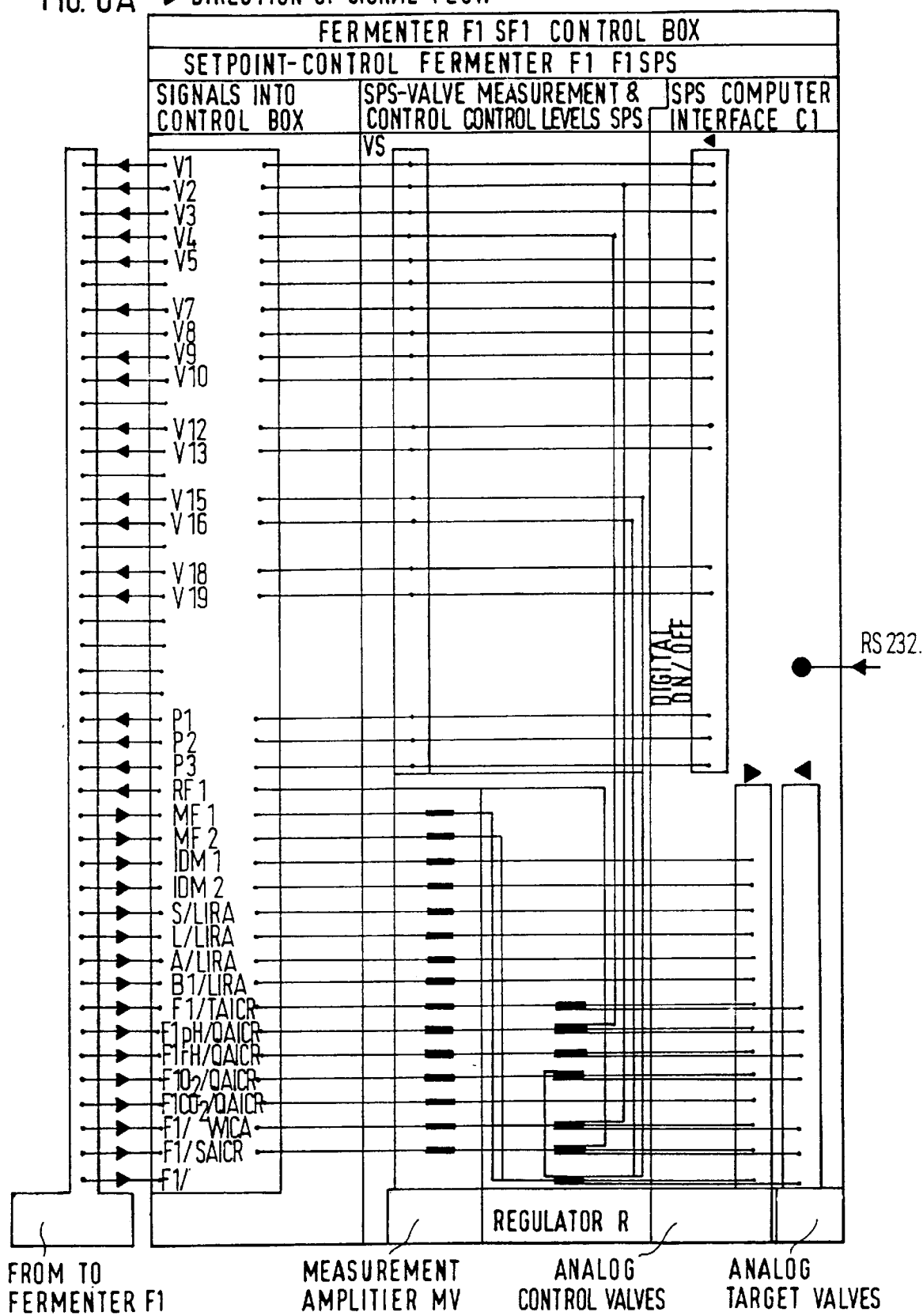
FIG. 6A ▶ DIRECTION OF SIGNAL FLOW

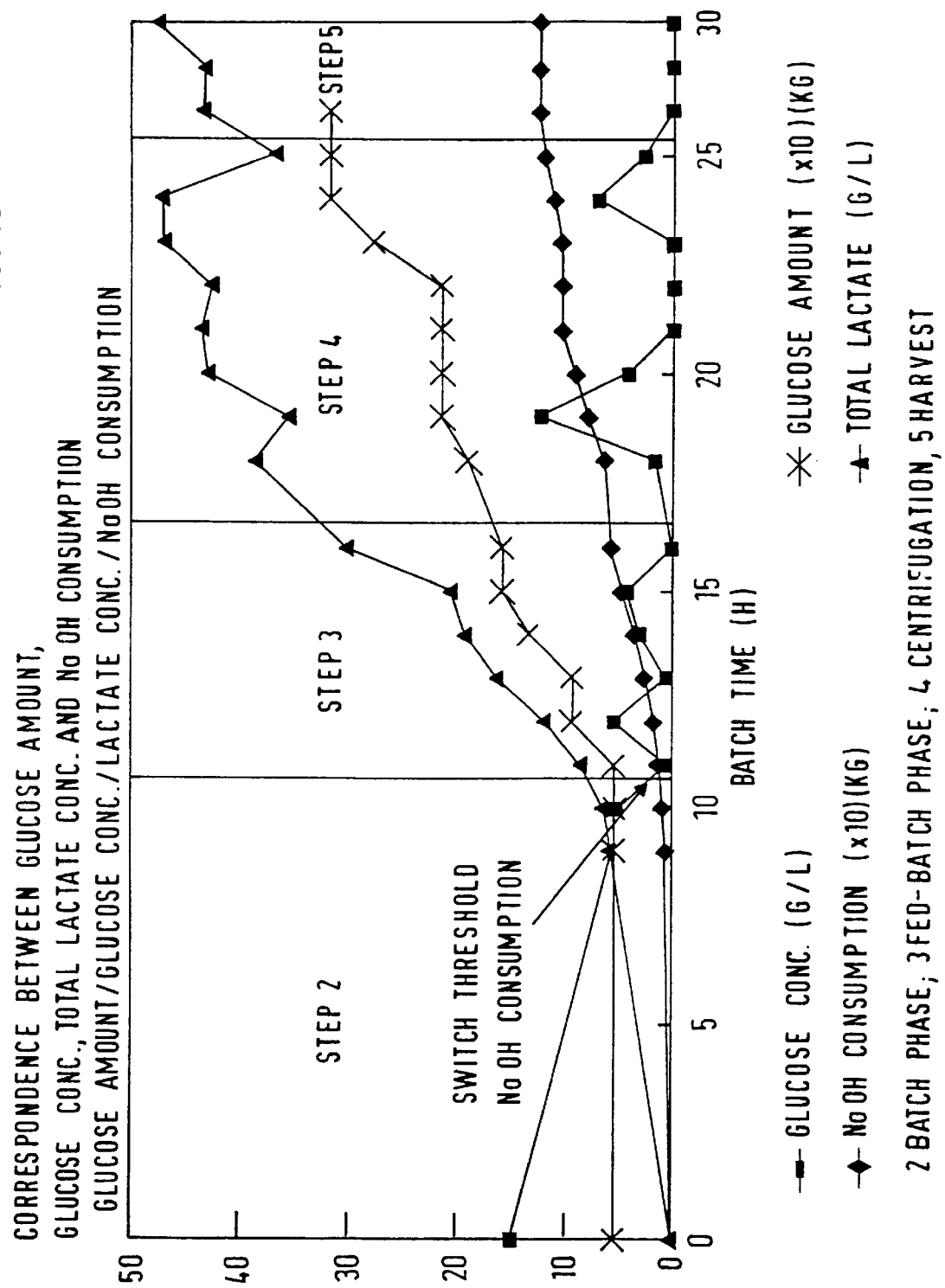

5,981,260

PROCESS FOR THE PRODUCTION OF CELL MASS AND/OR FERMENTATION PRODUCTS UNDER STERILE CONDITIONS

FIELD OF THE INVENTION

The field of the invention relates to a process for the production of cell mass and/or fermentation products.

INTRODUCTION

The invention relates to a process for the production of cell mass and/or fermentation products under sterile conditions in which the fermentation mixture, at least at times, is circulated and the metabolic products of the cultivated cells, and in some cases the cell mass itself, are intermittently or continuously separated; the invention also relates to an apparatus for implementing the process.

The use of fermenters in the biotechnology industry as a rule currently involves batchwise processes for preparation of fermentation solutions, production of biomass and manufacture of fermentation products. These batchwise procedures customarily include inoculation of a nutrient medium with the desired culture, cultivation for a specific time under precisely defined conditions, and harvesting of the microorganisms and/or recovery of the desired products of metabolism.

However, a number of disadvantages are associated with these batchwise processes. As a rule the medium at the starting concentration is sterilized in the filled fermentation tank. Heat sterilization of the medium entails high heating and cooling costs in installations with vessels which exceed 1,000 liters working volume. Holding the medium at 80 degrees Centigrade for long time periods often causes a loss of medium quality.

Sterilization generally requires several hours, which makes for a disadvantageous ratio between preparation time and working time. The shorter the actual fermentation time, the more disadvantageous this ratio becomes; it reaches 1:1 for brief fermentations.

In batchwise fermentations growth of microorganisms and living cells generally occurs under unfavorable conditions. At the beginning of the growth the cells require time (lag-phase) to adapt to the medium. In batchwise fermentations at the beginning of the process the viable cell count (inoculum viable cell count) is at its lowest level in the presence of the highest substrate concentration, which in many cases leads to substrate inhibition.

In the lag-phase the relationship between growth metabolism and maintenance metabolism is very unfavorable; the organism uses up substrate but does not grow. This means that there is poor substrate utilization in relation to cell yield and/or catabolite formation and/or biochemical transformation products.

The share of maintenance metabolism is also still high during the transition to the following phase of exponential growth.

The exponential phase of growth, in which maintenance metabolism is low in comparison to growth metabolism and there is optimal conversion of substrate by the cells, represents the optimal growth range.

However, in batch cultures, due to the increasing concentration of metabolic products, the exponential growth phase quickly comes to an end because of product inhibition, i.e., the concentration of the metabolic products produced by the cells becomes so high that growth initially slows down and eventually stops.

If the concentration at which product inhibition occurs is very low for certain cell types, or the rate of product formation per cell is very high, there is inhibition of growth and of metabolite production very early in the course of growth and poor yields are obtained. The time period during which greater amounts of metabolites are produced is likewise very short because of the shortness of the exponential growth phase. In batchwise production of cell mass or metabolites or transformation products the bulk of the product is produced at the end of the exponential phase of growth. Thus the fermenter has only a very brief phase of high productivity (high space-time yield).

As shown in FIG. 1, under the conditions described, about 50% of the biomass obtained in the process is produced in one hour. If the overall duration of the process, i.e., preparation, production, and equipment cleaning, is set at 24 hours, then the fermenter is only operated under optimal conditions for $1/24$th of its time in service.

BACKGROUND OF THE INVENTION

In the meantime several processes for the continuous fermentation of liquid substrates have become known. DE-A 33 23 205 describes a process and equipment for the continuous fermentation of a liquid substrate with simultaneous separation of the metabolic products formed in the fermentation. It is characteristic of this method that the fermentation mixture is circulated; during the circulation a thin stream of liquid flows over a membrane surface, and the circulating fermentation mixture is pressurized to the extent that the metabolic products formed are simultaneously selectively fractionated and separated from the fermentation mixture by filtration through a membrane. To maintain continuous operation a substrate supply cycle from which fresh substrate is continuously withdrawn and led into the fermentation cycle through a sterilization module is provided upstream. Metabolic products are continuously removed from the process.

This continuous process of the prior art, however, has a number of disadvantages, which are due to characteristics of construction as well as those connected with its operation.

In the process disclosed in DE-A 33 32 205, a membrane is used to remove the metabolic products produced from the fermentation mixture. Such membranes, however, tend to become blocked, which reduces the separation efficiency and requires very large membrane surface areas. In addition, special techniques and high pressure must be used to maintain the permeability of the membrane. Also, the membrane does not permit continuous removal of sediment from the fermentation equipment or continuous separation of the cell mass formed in the fermentation.

Additionally, this process of the prior art has a number of the disadvantages described above for the batchwise process. These disadvantages in particular relate to sterilization of the equipment and media and additionally the inability to adapt the culture conditions to the prevailing growth phase of the microorganism. This disadvantage results in a diminished yield of cell mass and/or catabolite formation and simultaneously poor substrate utilization, and also leads to unacceptably long culture times.

SUMMARY OF THE INVENTION

The object of the invention is therefore to establish a process of the type described above, in which the following are possible in continuous, semi-continuous, or batchwise operations: optimal adaptation of culture conditions to the growth phase of a microorganism which is being cultured, optimal regulation of cell mass and/or catabolite formation, and optimal utilization of the nutrient medium for the purpose at hand.

This object is accomplished as described above, involving the following steps:

Charging the fermentation equipment with a sufficient amount of nutrient medium to start the desired cell culture;

Sterilizing the equipment as well as adjusting the desired concentration of the nutrient medium;

Inoculating the nutrient medium with the starter culture and permitting undisturbed growth of the culture for a definite time period;

Increasing the concentration of the nutrient medium to the specific nutrient medium concentration of the cell culture, with simultaneous increase of the volume of the nutrient medium to the working volume of the equipment, and increase of the cell concentration as well;

Transition to the continuous procedure with exchange of the nutrient medium, separation of the products of metabolism, and complete or partial recycling of the cells;

Terminating the continuous procedure at a desired time and harvesting the cell mass under sterile conditions; and possibly Repeating some or all of the above-mentioned steps consecutively.

BRIEF DESCRIPTION OF THE FIGURES

FIG. 2. Comparison of time and energy requirements for the sterilization of different liquid volumes in a 5,000 liter fermenter;

FIG. 3. The average growth rate $\mu$ as a function of the initial glucose concentration in a medium for *Lactobacillus curvatus* S3;

FIG. 4. The curve of the specific growth rate $\mu$ during linear and exponential cell growth;

FIG. 5. A fermenter according to the invention with cell recycling via a separator;

FIG. 6A. Control of the fermenter according to the invention with cell recycling via a separator, partial view for extension onto FIG. 6B;

FIG. 10. Corresponds to FIG. 8.

DETAILED DESCRIPTION OF THE INVENTION

Figure 1:
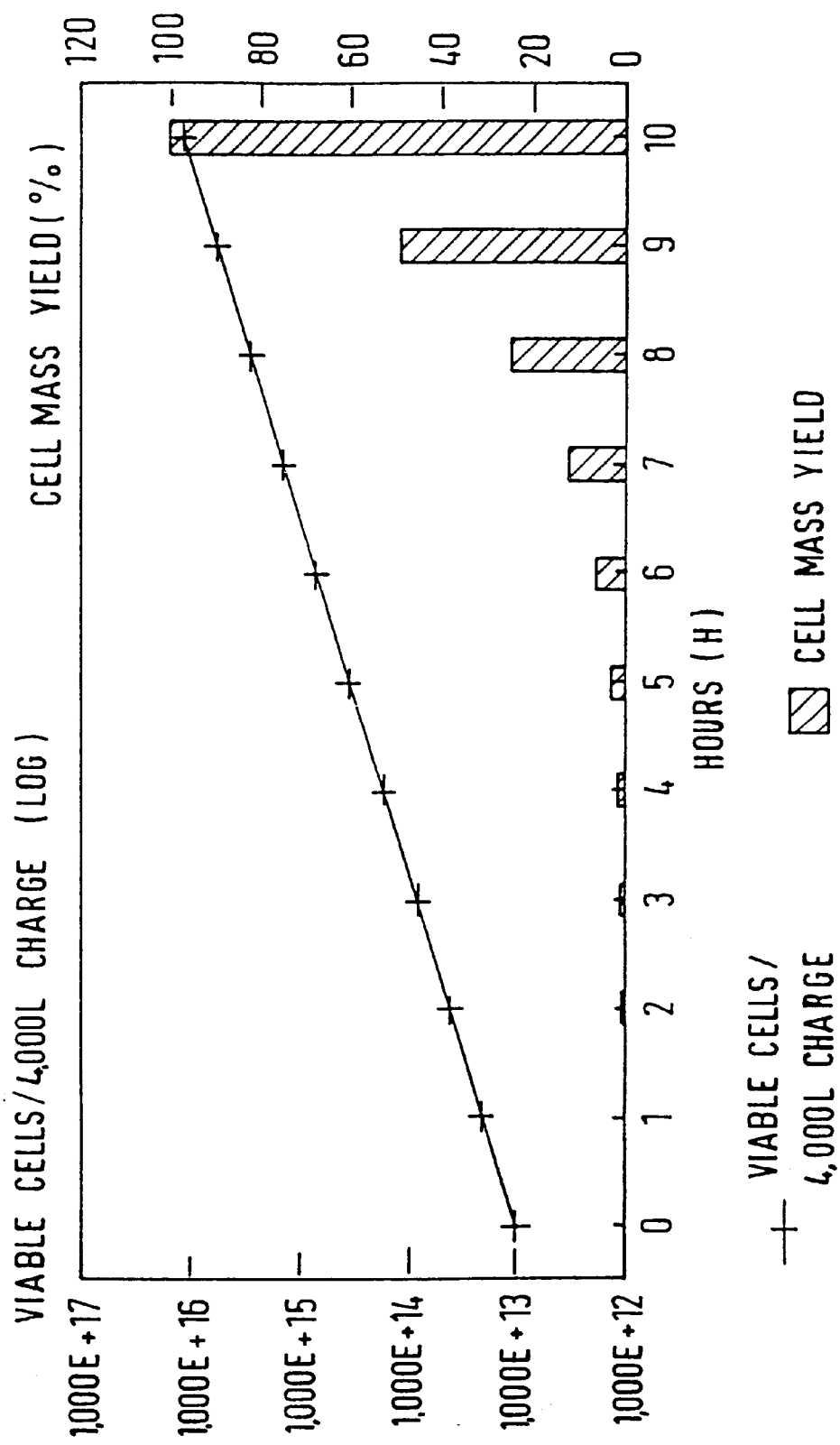
FIG. 1. Cell mass yield per unit time for *Staphylococcus carnosus* Sc1.

The object of the invention is therefore to establish a process of the type described above, in which the following are possible in continuous, semi-continuous, or batchwise operations: optimal adaptation of culture conditions to the growth phase of a microorganism which is being cultured, optimal regulation of cell mass and/or catabolite formation, and optimal utilization of the nutrient medium for the purpose at hand.

This object is accomplished as described above, involving the following steps:

Charging the fermentation equipment with a sufficient amount of nutrient medium to start the desired cell culture;

Sterilizing the equipment as well as adjusting the desired concentration of the nutrient medium;

Inoculating the nutrient medium with the starter culture and permitting undisturbed growth of the culture for a definite time period;

Increasing the concentration of the nutrient medium to the specific nutrient medium concentration of the cell culture, with simultaneous increase of the volume of the nutrient medium to the working volume of the equipment, and increase of the cell concentration as well;

Transition to the continuous procedure with exchange of the nutrient medium, separation of the products of metabolism, and complete or partial recycling of the cells;

Terminating the continuous procedure at a desired time and harvesting the cell mass under sterile conditions; and possibly Repeating some or all of the above-mentioned steps consecutively.

Preferred procedures are the object of the subsidiary claims.

The process according to the invention can be used for any microorganism which can be cultured in conventional fermenters. The usual culture conditions and nutrient media are used; the advantage of the process described in the invention is the particular operating procedure rather than the use of unusual conditions or media. If high speed stirring or centrifugal separation are used according to the invention, organisms which are not sensitive to shear are preferred.

The process according to the invention can be used to cultivate bacteria and fungi of the most diverse types. The process is particularly suited to the cultivation of aerobic as well as anaerobic bacterial and Gram-positive as well as Gram-negative bacteria. Particularly noteworthy are the various cocci, particularly micrococci, planococci, deinococci, staphylococci, stomatococci, streptococci, leuconostoc, pediococci, aerococci, gemella, peptococci, peptostreptococci, ruminococci, cuprococci, as well as the genus Sarcina. In addition, bacteria in the genera Bacillus, Sporolactobacillus, Clostridium, Desulfotomaculum, Sporosarcina, Planococcus, Lactobacillus, and Korthia. In addition, bifidobacteria, brevibacteria, bacteria in the genera Zymomonas, Acetobacter, Gluconobacter, Pseudomonas, Vibrio, and Aeromonas are also suitable. In addition, Gram-negative anaerobic bacteria in the genera Escherichia, Shigella, Edwardsiella, Citrobacter, Salmonella, Klebsiella, Enterobacter, Hafnia, Serratia, Proteus, Providencia, Morganella, Yersinia, Erwinia, Obesumbacterium, Kluyvera, Cedecea, Tatumella, Xenorhabdus, and Rahnella are noted. Gram-negative aerobic rods and cocci which are suited to the process according to the invention are those in the Pseudomonadaceae, Azotobacteriaceae, Rhizobiaceae, Methylococcaceae, Halobacteriaceae, Acetobacteriaceae, Legionelllaceae, and Neisseriaceae families.

The process according to the invention is suitable for the multiplication and production of the cultivated microorganisms, which can be separated from the process and subsequently used for a different purpose, as well as for obtaining the metabolic products produced by the microorganisms. The yield of microorganisms or of metabolic products can thus be optimized in a simple manner, i.e., by establishing a work stage which utilizes the maximal multiplication rate, or else utilizes the optimal substrate transformation by the microorganism. The process according to the invention thus enables the establishment of work stages in which the share of substrate utilization in maintenance metabolism is small, which is important for the production of cell mass, or work stages with a high proportion of maintenance metabolism and little cell production, which is important for the production of metabolic products. Furthermore, in the process the culture medium is utilized to the fullest extent, and at the same time metabolic products are removed, thereby avoiding substrate inhibition.

The process according to the invention is divided into 5 steps, which run cyclically after equipment start up, and are subdivided into the following process engineering requirements.

1. Preparation and sterilization of the fermentation equipment and the components of the nutrient medium;
2. First work cycle of the equipment in batchwise process mode with low medium concentration and partial filling;
3. After a specific medium concentration is attained, transition to controlled medium dispensing until the final fermentation volume is reached;
4. Transition to continuous process mode with nutrient medium exchange and complete or partial cell separation;
5. Termination of the continuous fermentation segment and harvest of the total biomass under sterile conditions; and
6. If necessary, readdition of sterile nutrient medium to the sterile equipment and repetition of the process according to Steps 1 through 5 with reduction of overall sterilization time and energy requirements.

In Step 1 the entire equipment is sterilized by heat sterilization of a concentrate of the medium in the production kettle. As soon after sterilization as the temperature of the concentrate falls below 100 degrees Centigrade, it is quickly cooled to the fermentation temperature and diluted by the direct injection of cold, filtration-sterilized water, after which media which can be sterilized by filtration are added. This process saves the heat energy required for the heat sterilization of the total volume of the medium, and provided that the hot and cold phases are mixed in the proper relationship it saves the cooling energy for cooling the total fermentation volume from temperatures close to 100 degrees Centigrade to the fermentation temperature; the time which would be needed for cooling the total fermentation volume in a stirred, jacketed kettle is also saved, since the time required to cool the concentrate by the direct injection of sterile water is short in comparison.

FIG. 2 presents a comparison of the time and energy requirements for the sterilization of a 5,000 liter fermenter containing different sterilization volumes. Approximately 25% of the time and approximately 75% of the amounts of water, gas, and electricity are saved.

With start up of the equipment as a batchwise procedure with low medium concentration according to Step 2, the cells are optimally adapted to their substrate and have a high growth rate, since at the correspondingly low medium concentration niether substrate nor product inhibition occur. In contrast, in the usual batchwise procedure the medium concentration is set at a high level to provide high yields, leading to substrate inhibition at the outset and resulting in worsened growth and diminished yields of cell mass, catabolites, and transformation products.

FIG. 3 shows the dependence of the average growth rate $\mu$ of the strain *Lactobacillus curvatus,* representing the other microorganisms, on the glucose concentration in the growth medium. The higher the glucose concentration of the medium, the lower the average growth rate $\mu$, i.e., the average growth rate $\mu$ increases at low glucose concentration.

In Step 3, medium is dispensed into the fermenter in response to the utilization of a limiting substrate or according to a defined formula, thereby increasing the volume. The increasing cell concentration continuously is diluted by medium addition, so that product inhibition does not occur. The concentration of the medium dispensed is adjusted to ensure that the overall medium concentration, when the final volume of the fermenter is reached, is such that the ratio of the percent share of the growth metabolism maintenance metabolism does not exceed a value which is valid for the particular cell being cultivated.

Step 3 is an improvement over the batchwise process in that the amount of added medium increases during cell growth and the material concentration of the medium is held essentially constant. This produces exponential cell growth throughout the entire step. In the conventional batchwise process the amount of substrate decreases during cell growth and the material concentrations are variable. This is inimical to ideal cell growth. An additional advantage of Step 3 is the very good utilization of substrate in this process segment, because substrate is dispensed in response to requirement.

In the process according to the invention in Step 4 there is a medium exchange when the final fermentation volume is reached.

The medium is removed with a sterile separation system, preferably with a centrifuge operated under sterile conditions. According to the first variation, 4a, all the cells are returned to the process. The spent medium separated from the system is replaced with an identical volume of fresh medium. The concentration of the medium dispensed is set below the concentration which causes substrate inhibition, so that there is substrate limited growth of the cell mass.

To ensure maximal substrate utilization, transition from the batchwise to the continuous procedure proceeds as follows. At the beginning of the continuous step, the amount of medium dispensed is calculated from the specific utilization of the limiting substrate or from the growth curve, while the rate of medium volume exchange from the start of the continuous step is held as high as possible. This leads to dilution of the medium at the beginning of the continuous step and to enhanced washout of metabolic products, thereby promoting further cell growth.

As growth continues the media requirements increase with cell mass until the amount of medium addition reaches the optimal range for continuous operation. When this time is reached the amount of medium dispensed is held constant, and the system is in a stable state of substrate limitation.

The specific growth rate $\mu$ of the cells, which remains at essentially the same value until the optimal continuous range of operation is reached, decreases exponentially during the course of operation in this range, while the viable count increases linearly.

FIG. 4 shows the course of the specific growth rate $\mu$ during linear and exponential cell growth. There is a significant difference between the time required for an exponentially growing organism to reach a specific viable count and the time required by the same organism growing linearly. A culture grows linearly if the addition of nutrient medium or the availability of the nutrient medium is linear rather than exponential. In linear growth the growth rate $\mu$ decreases exponentially with increasing cell count. Thereby maintenance metabolism has a very large share in the overall metabolism. The value of $\mu$ at which partial separation is begun is determined experimentally.

According to a second variation, 4b, the process according to the invention in Step 4 is run with partial separation of the microorganisms, for instance in biochemical transformations. In this case in Step 4 a cell mass concentration is reached at which the growth rate $\mu$ is at the point of maximal transformation rate. At this point cell mass removal from the system is started. This maintains a constant cell concentration in the system. Thereby the system is kept at a defined workstage with a maximal transformation rate.

Step 5, with termination of the continuous fermentation step, leads to variation 4a if the growth rate $\mu$ reaches a lower limit. As a rule this limit follows from the metabolic physiology of the cells, which have different characteristics depending on later addition.

In harvesting a culture according to 4a the whole biomass is separated out. In principle this step represents a batchwise procedure, but it differs significantly in regard to the cell mass yield. In the process according to the invention the yield is significantly greater than in the conventional batchwise process.

The yield from a batchwise procedure (Step 4a) is important for processes in which the product must be defined from a legal or process technology standpoint as CHARGE, for example in the pharmaceutical or food industry. The process according to the invention has the advantage in respect to cell yield of being a continuous process with cell recycling as well as the advantage of providing an unambiguous CHARGE definition. In each case harvesting is accomplished under sterile conditions.

In Step 4b, on the other hand, a fully continuous fermentation process is described, the termination of which in Step 5 is not due to the growth kinetics of the cell mass, but rather to external circumstances such as contamination, defective equipment components, or deliberate termination.

After harvesting in Step 5 the part of the equipment which was in contact with the product is washed with filtration-sterilized water, filled from the dispensing tanks with medium which had been sterilized shortly before, and thereby immediately made ready for the next run. This run is again inoculated with one of the starter cultures in the exponential phase and the process is repeated.

In the process according to the invention, the production fermenter is only sterilized at the outset or after contamination; in subsequent runs only the storage tank need be sterilized. If necessary the medium can be filled hot into the fermenter, where it can quickly be cooled down by the direct injection of water.

The invention further relates to a device for implementing the process according to the invention which comprises the following: a sterilizable fermentation kettle, at least one tank to receive and heat sterilize one of the medium components which cannot be sterilized by filtration, and/or at least one storage vessel with a sterilizing filter to receive a medium component which can be sterilized by filtration and which has a sterilizing filter for the continuous production of sterile medium components, a sterilizable circulator connected to the fermentation kettle and equipped with fittings for the separation of exhausted nutrient medium and metabolic products, and a centrifuge for the separation and isolation of cell mass and exhausted nutrient medium.

Preferred implementation procedures with this device are the object of the subclaims.

The device according to the invention and its operation are described below with reference to the accompanying FIG. 5.

Figure 6B:
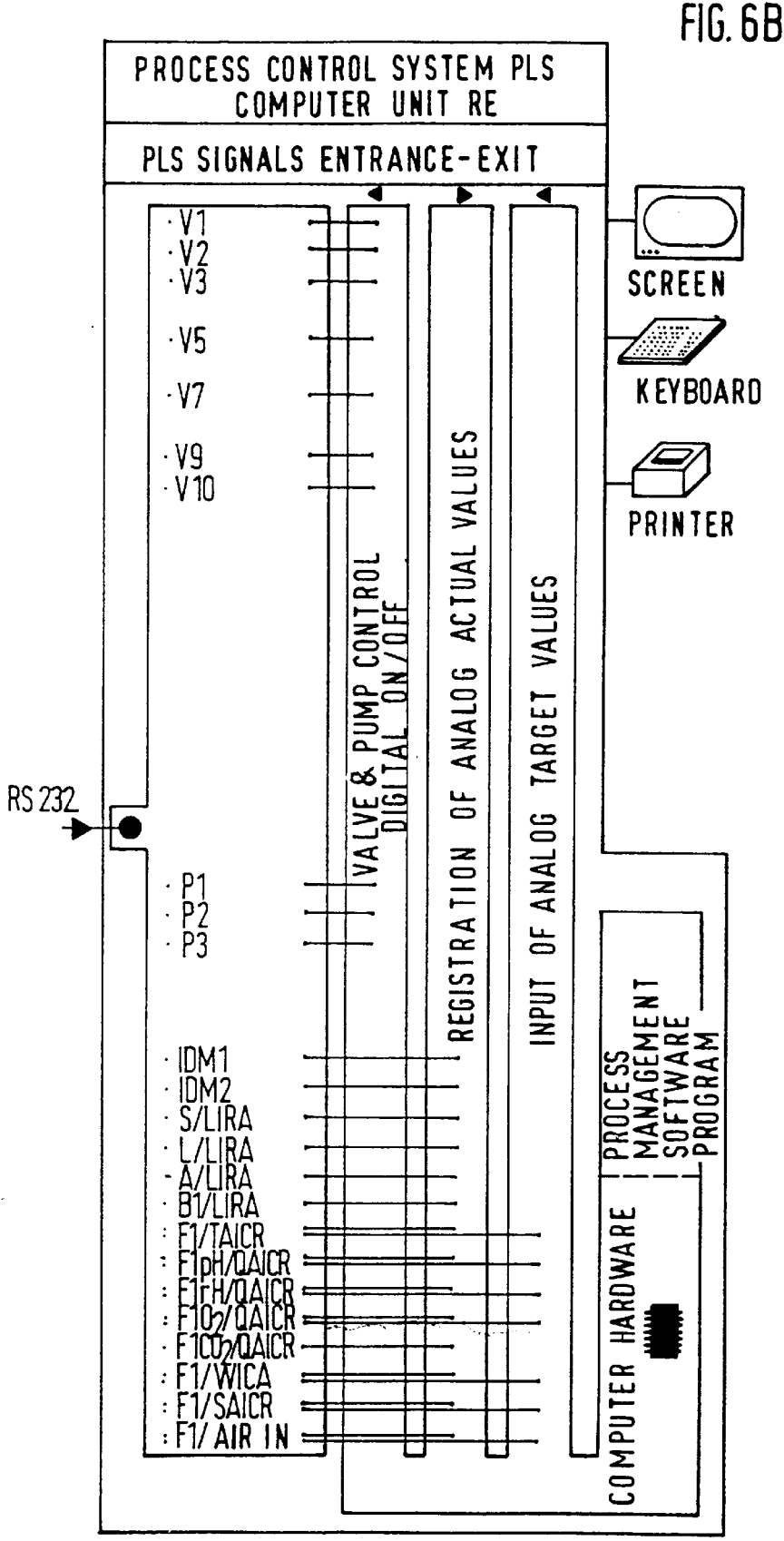
FIG. 6B Control of the fermentator according to the invention with cell recycling via a separator, partial view for extension from FIG. 6A.

The fermenter F1 is aerated with filtration-sterilized air LF1 and is coupled to the centrifuge Z1 by a circulator which can be sterilized with steam. Pump P1 returns the concentrate separated in Z1 to F1. The fermenter F1 is alternatively filled from tank B1 and/or via the sterilizing filter S1 with filtration-sterilized medium or directly from tank B1 with heat-sterilized medium. The medium storage vessels S and A are filled with medium in the same way. The medium storage vessel S may in addition be filled with filtration-sterilized medium via the sterilizing filter M1. An integrated process control system, which is responsible for measurement, control and regulation of the complete installation is specifically programmed by the software and schematically shown in FIGS. 6A and 6B.

The process according to the invention consists of the six previously cited steps, which are described in greater detail below. Steps 1 through 6 are illustrated in FIG. 5.

Step 1 includes the preparation and sterilization of the fermentation equipment and the medium components and consists of six subsidiary steps.

1.1 Provision of processing water in storage tank F1 and filling storage tanks F1 and B1 with medium.

1.2 Heat sterilization in F1 of medium concentrate which cannot be sterilized by filtration.

1.3 Direct injection of sterile cooling water into F1 through the sterilizing filter S1.

1.4 Transfer of filtration-sterilized medium from storage tank B1 into the fermenter F1 and the media storage vessels S and A.

1.5 Adjustment of the fermentation volume in F1 with sterile water from S1. 1.6 Refilling B1 with concentrate composed of medium components which cannot be sterilized by filtration, and heat sterilization of B1 followed by indirect cooling with water.

In Step 1.1 sufficient water to dissolve the media components is filled into the fermenter F1 and the storage tank B1 through the main process water supply valves V17 and V18. Both vessels are filled with media through the handholes H1 and H1 and the medium is freed of lumps by stirring with stirrers RF1 and RB1. At this point both vessels contain medium concentrate.

The medium concentrate in F1 is heat-sterilized in Step 1.2 with the heating mantle HM1 and cooled to below 100 degrees Centigrade.

In Step 1.3 sterile process water is injected through valve V2 and sterilizing filter S1 under stirring until the temperature of the mix reaches approximately 60 degrees Centigrade.

Sterile medium is then transferred through valve V11 on vessel B1 and the sterilizing filter S1 into the fermenter F1. Likewise in Step 1.4 filtration-sterilized medium is transferred into the medium storage tanks S and A through valves V12 and V13.

In the following Step 1.5 the fermenter F1 is brought to the starting volume with sterile process water from the sterilizing filter S1 through valve V2. At this juncture the fermenter is filled to approximately ¼ to ⅓ of the maximum working volume. The medium concentration for the start of the process is adjusted, and the temperature is between 30 and 35 degrees Centigrade, which as a rule is close to the process temperature.

In Step 1.6 storage tank B1, which is empty and washed, after receiving process water through valve V17 is filled through handhole H2 with medium components which cannot be sterilized by filtration and the concentrate is sterilized with the heating mantle H2 and cooled indirectly with water. The medium components stored in vessel B1 and medium storage vessels S and A are used in subsequent steps for dispensing medium. Step 2 includes the first work cycle of the equipment in the batchwise procedure with low medium concentration and partial filling, and consists of four main steps.

2.1 Activation of the process control system PLS.
2.2 Inoculation of the fermenter F1.
2.3 Cell growth.
2.4 Switching to Step 3 on the basis of the above-mentioned criteria for switching.

The process control system PLS monitors and controls the overall process. It consists of the computer unit RE, the keyboard TA, the screen Bi, and the printer Du. The process control system is bidirectionally connected through the data interface RS232 to the computer interface of the setpoint control fermenter F1 SPS; through control of the valve controller SPS VS it directly or indirectly controls regulator R, valve V and the pumps P in accordance with the target values. All values measured in the process are transmitted to the process control system PLS through the amplifier MV, the computer interface CI and the data interface R232. Before the process is started the process-specific software is loaded. This software includes all alarm values, target values, analytical functions, data for controlling the valves, and the documentation. The starting conditions for the process are transmitted by the PLS and include, for example, establishment of the following parameters for F1:

Process temperature
pH values
Redox potential
Partial pressure of oxygen
Weight
Stirrer speed Valves V1, V2, V3, V5, and V7, which are under control, are closed; the equipment is ready to be inoculated.

The fermenter F1 is inoculated through the inoculation nozzle AS with the starter culture, prepared in advance, and the process is started by the process control system PLS, i.e., the process control and monitoring functions are activated.

In the initial phase of the process (Step 2.3), cell growth is in accord with a batchwise process. The advantage in the process according to the invention is the low medium concentration, which permits optimal cell multiplication and good adaption of the cells to the medium.

At the end of the batchwise growth phase, before substrate limitation is reached, it is necessary to switch at a switch criterion to the next step in the process, medium dispensing. Establishment of switch criteria is described below with several examples.

A homofermentative strain of Lactobacillus, which converts glucose essentially quantitatively to lactic acid, serves as an example of establishment of a switch criterion by the stoichiometric titration of metabolite production.

The pH of the fermenter is held constant during the cultivation of lactobacilli, i.e., the falling pH due to lactic acid formation is held constant by titration with a solution of alkali of defined normality. The pH value in the fermenter F1 is measured and controlled with the pH-controller pH QAICR, which consists of a measuring probe MS, a measurement amplifier MV, and a regulator R. The measured value and the target values are interchanged in the process control system PLS as described above. The alkali solution in the medium storage tank L is dispensed into the fermenter F1 by the pH regulator F1 pH QAICR through valve V4. Utilization of the alkali solution in the medium storage tank L is measured with a capacitive fluid level probe LIRA and the data are processed by the process control system PLS.

The switch threshold is defined as the total amount of alkali solution used. The switch threshold is established in preliminary experiments in which the cells are grown in the growth medium into the stationary phase, the utilization of alkali solution is determined, and the amount of alkali solution used corresponding to the amount of residual substrate (glucose amount) present when the cells are in the exponential growth phase and not yet under conditions of substrate limitation is calculated. The calculated amount of alkali solution is thus less than that actually used.

A strain of micrococcus (aerobic strain) serves as an example of the establishment of a switch criterion based on a requirement for air. The partial pressure of oxygen is kept at a constant value during growth in Step 2. The $O_2$ controller $O_2$ QAICR consists of a measuring probe MS, a measurement amplifier MV, and a controller R. The measurements and target values are interchanged by the process control system PLS as described in 2.1. The output of the controller R activates the control valves V15 and V16, which control the quantity of gas fed into the system.

During batchwise growth the cells use increasingly more air, measured with the bulk flow meter MF1 and MF2.

This applies as long as substrate is present and the cells are multiplying. When the cells enter conditions of substrate limitation, the requirement for air under constant oxygen partial pressure, controlled by $F1-O_2$-QAICR and constant speed stirring (controlled by SAICR) decreases. This decrease is used as a switch threshold.

A strain of leuconostoc serves as an example of the establishment of a switch point based on the $CO_2$ content of the liquid or gas phase.

During batchwise growth the cells produce $CO_2$, which dissolves in the medium and is measured with the $CO_2$ measuring instrument $F1-CO_2$-QAIC, consisting of the measuring probe MS and the amplifier MV. To detect changes in $CO_2$-concentration more quickly, the fermenter is purged with nitrogen through the bulk flow gauge and stirred at constant speed to eliminate $CO_2$. When the cells enter conditions of substrate limitation, the partial pressure of $CO_2$ in the medium decreases. This decrease is used as a switch threshold.

In Step 3 there is transition to regulated or controlled medium dispensing until the final volume of the fermentation is reached; it consists of two main steps:

3.1 Dispensing medium.
3.2 Switching to Step 4 on the basis of the switch criteria specified above.

Regulated dispensing of medium begins as soon as the switch criteria are fulfilled. To this end, the amount of alkali solution used for pH control during the preceding 2 to 10 minutes is determined by the liquid level meter LIRA in the medium storage vessel L, and is converted by the process control system to the amount of limiting substrate (e.g., glucose) to be dispensed. This conversion is done according to the following formula.

$$SD_{Bed.Glc} = \frac{K_i \times k_3 \times 0.5 \times Z \times a \times 180 \text{ g/mol}}{k_2 \times t_1}$$

in which
z=alkali solution used in liters
a=normality of the alkali solution (molar)
$t_1$=time required for alkali solution use (minutes)

$k_1$=correction factor for undissociated acid in culture pH measurements $k_2$=substrate utilization factor for the particular culture $k_3$=factor for previous addition $SD_{Bed.Glc}$=amount of glucose to be dispensed in (grams/minute).

There is a definite relationship, which is determined in preliminary experiments, between the limiting substrate and the other substrate components. The process control system calculates the amounts of the other substrate concentrates and the amount of water needed for dilution to the working concentration.

Medium concentrate is dispensed at 2 to 5 minute intervals. The medium components which can be sterilized by filtration are dispensed from the medium tank S through valve V5, those which can be heat-sterilized are dispensed from tank B1 through valve V1, and the water diluent is dispensed through the filtration sterilizer S1 and valve V2. The volumes of media dispensed from medium tank S and tank B1 are determined with the liquid level gauge LIRA. The weight controller WICA controls diluent water dispensing through the filtration sterilizer S1, while an increasing target weight is programmed for fermenter F1 by the process control system PLS.

Utilization of the limiting substrate as well as of the total medium increases with increasing cell mass. Since the medium concentration is held constant, in any dispensing cycle the amount of medium dispensed increases constantly until the maximum capacity of the fermenter is reached. The concentration of the dispensed medium is chosen so that there is a maximal cell yield under the given conditions of operation when the maximal capacity of the fermenter is reached. This value is the maximal or the specific cell yield.

Medium dispensing for organisms for which no limiting substrate during culture has been specifically determined is controlled with a shell curve, corresponding to an exponential function which is characteristic of the growth of a specific organism. The specific substrate requirement per $1 \times 10^{12}$ cells, the specific growth rate $\mu$, the viable count reached at the time of the switch threshold in Step 2, and the medium concentration at the maximal attainable viable count are determined in preliminary experiments.

As soon as the switch criterion described in Step 2.4 is reached, controlled medium dispensing begins. The amount of medium necessary to reach a viable count of $1 \times 10^{12}$ cells is defined as medium amount 1, and is strain specific.

The concentration of the medium to be dispensed is held constant and so adjusted that when the maximal fermenter capacity is reached the total amount of medium is that which provides maximal cell yield under the given conditions. During cultivation the substrate volumes for each dispensing cycle increase.

The amount of substrate dispensed is calculated according to the following equations.

$$xt = e^{\mu \times t + \ln xo} \quad (3.1.2.a)$$

$$SD = sS \times X_t \quad (3.1.2.b)$$

$$SD_{Ber} = sS \times e^{\mu t + \ln xo} \quad (3.1.2.c)$$

$X_o$=total viable count in the system at the start of dispensing $x_t$=total viable count in the system at time t $\mu_o$=specific growth rate at the start of dispensing t=time interval between $X_o$ and $X_t$ sS=specific substrate requirement for $1 \times 10^{12}$ viable cells in grams or milliliters $SD_{Ber}$=calculated amount of substrate to be dispensed.

Calculation of the amount of substrate to be dispensed and dispensing is done every 5 to 15 minutes. If too small volumes are dispensed, they are made up during the next dispensing cycle; too great volumes are compensated for dispensing minimal amounts.

If the oxygen requirement of the cells dispensed by the bulk flow meters MF1 and MF2 under constant speed stirring remains constant or falls for a specific time due to substrate limitation, the amount dispensed is increased, thereby abolishing the substrate limitation. If the limitation is still not eliminated after a one time increase in $\mu$, after a time interval specified by the process $\mu$ is again increased.

The control function of the process can be adapted to the $CO_2$ partial pressure, determined by the $CO_2$ meter $CO_2$QAICR, as well as to the partial pressure of oxygen. The principle of the measurement is described under Step 2.4.3. If, due to substrate limitation, the partial pressure of the $CO_2$ measured by the bulk flow meter $MF_2$ under constant speed stirring by the stirrer RF1 and a constant amount of nitrogen blown into fermenter F1 does not increase or decreases, the software of the process control system PLS increases the amount dispensed sufficiently to speed up dispensing of nutrient medium and abolish the substrate limitation. If the limitation is still not abolished after a one time increase in $\mu$, the software of the process control system PLS again increases $\mu$.

The weight of the fermenter F1, measured with the scale F1 WICA, determines the switch criterion between Steps 3 and 4. The weight threshold is determined according to process specifications.

Step 4 includes transition to continuous procedure with nutrient medium exchange and complete recycling of cells or partial cell separation and comprises four main steps.

4.1 Centrifuge start up and start of the separation with cell recycling, 4.2 Procedure with complete recycling.

4.2.1 Dispensing of substrate during cell recycling, alternatively.

4.3 Procedure with partial cell separation, 4.3.1 Process operation with complete cell recycling until the start of partial separation, 4.3.2 Switching to partial cell separation, 4.3.3 Partial separation, and also, 4.4 Termination and switch to Step 5.

Before the switch threshold according to Step 3.2 is reached the separator Z1 is started up; after the switch threshold is reached valve V7 is opened by the process control system PLS. Before separation is started the separator is set at the maximal flow rate by valve V8. The flow rate set is measured by the inductive bulk flowmeter IDM 1 and recorded by the process control system PLS. To recycle the separated cell mass the pump P1 is switched on in parallel with valve V7. Valves V9 and V6 are open at the start of the process.

The consistency of the separated cell mass must be fluid so that it can be recycled through pump P1 according to Step 4.2 and quickly remixed in the fermenter. As a rule the consistency is suitable when the sediment content is less than 60%. The sediment content must not decrease to less than 40%, since at lower degrees of thickening the volume of the recycled medium reduces the effective separation efficiency of the separator Z1 to 15%.

The degree of thickening is controlled by the emptying time of the separator Z1. Emptying occurs at 3 to 4 minute intervals because the cells must not be held in the separator any longer. Depending on the type of cell, these conditions minimize cell damage.

Dispensing of substrate is continued, depending on the chosen parameters, during cell recycling; if necessary it is interrupted while cell recycling is carried out.

Cell recycling without medium dispensing is necessary for organisms which only sediment well in media which are completely glucose free. The following is an example of organisms which can be recycled during culture with medium dispensing.

Substrate dispensed in response to the utilization of a limiting substrate is added as required. Diluent water is dispensed through the sterilizing filter S1 and valve V2, controlled by the weight regulator WICA of fermenter F1, which holds the weight of the fermenter constant independently of the separation efficiency of the centrifuge Z1 running under the prevailing conditions. The preset target weight corresponds to the working weight in fermenter F1 specified by the process. The amounts of concentrated medium dispensed from medium tank S through valve V5 and from vessel B1 through valve V1 are determined according to and dispensed in response to utilization of the limiting substrate. The course of the total substrate amount added and of the time dependent amount of substrate dispensed in the process represents an exponential function up to the upper limit, from which point dispensing is linear rather than exponential. The upper limit is calculated from the maximal possible medium concentration of the input, which must not exceed a value determined in preliminary experiments.

This maximal input amount is dependent on the effective separation efficiency Teff of the centrifuge running under the prevailing conditions. The amount of substrate dispensed in response to requirement is always less than or equal to the maximal amount calculated from Teff.

With the control system according to the invention the viable count attained is at least a factor of ten greater than that from a conventional batchwise process.

Dispensing can also be driven by previously calculated values (shell curve) analogously to the dispensing in accord with utilization of a limiting substrate described above.

The first part of the procedure with partial cell separation (Step 4.3) represents the process with complete cell recycling described in 4.2. To start partial cell separation the process is brought to the work stage of complete cell recycling.

Although the switch criterion for starting partial cell separation is specific for the process, it is still coupled to the specific growth rate a, since substrate utilization and production of metabolites are directly dependent on the specific growth rate. $\mu$, which is specific to the organism, is determined in preliminary experiments.

The total viable count in the complete system is calculated from the amount of substrate added to the system and the specific substrate requirement per cell count. For a definite system volume this corresponds to a definite maximal medium concentration and for a definite separation capacity to a definite growth rate, $\mu$, which represents the switch point.

The viable count reached in the system at the time of partial separation is kept constant by withdrawal of a cell mass stream from the system.

To withdraw cell mass from the system, while pump P1 is running valve V9 is closed and valve V10 is opened. The amount of concentrate drawn off is registered by the bulk flowmeter IDM2, and valve V10 is closed and valve V9 is opened when the calculated amount is reached. A withdrawal cycle lasts from 3 to 10 minutes.

When substrate is dispensed in response to a limiting substrate, dispensing is continued under the conditions prevailing at the start of the partial separation. When dispensing occurs at the upper limit it is continued at the same level.

Substrate dispensed in response to precalculated values (shell curve) is likewise continued under the conditions prevailing at the start of the partial separation. When dispensing occurs at the upper limit, it is continued at the same level.

This dispensing level results in replenishment of the separated cell mass by renewed growth. A stable equilibrium is established in the system by maintaining a constant relationship between influx and outflow. The cells grow at a constant growth rate $\mu$.

The termination criterion in the continuous step of the process with partial cell separation is based on total substrate amount. In the presence of a total substrate amount, as specified by the process, the total number of viable cells specified by the process is formed in the system which has a defined growth rate $\mu$. Substrate utilization is defined as no longer adequate when the growth rate is below a specific value.

The termination criterion in the continuous step of the process with partial cell separation is based on system failures such as contamination, fouling, or mechanical faults, or is due to economic or other considerations.

Step 5 involves termination of the continuous fermentation segment and harvesting of the total biomass under sterile conditions.

Organisms whose sedimentation properties permit satisfactory harvesting only in glucose free medium are harvested without substrate dispensing and at the maximal separation efficiency of the centrifuge.

Batches in which substrate is dispensed in response to the limiting substrate or to a shell curve are harvested identically, yielding cell mass which retains metabolic activity. Harvesting is started by opening valve V1 and closing valve V9. The harvest described above produces a time-dependent weight loss of the fermenter F1AMF1, controlled by the weight controller WICA F1, resulting from the maximally allowable harvest time; this weight loss must be less than the maximal separation efficiency of the centrifuge, measured by IDM1.

Step 6 consists of the readdition of sterile medium to the sterile equipment and repetition of the process according to Steps 1 through 5 with savings in total sterilization time and energy (split batch operation).

Immediately following harvesting all valves are closed. Fermenter F1 is washed with filtration sterilized water from the sterilizing filter S1 through valve V19 and the CIP sphere to remove fouling deposits (fouling) which may be present. The dirty water is piped into centrifuge Z1 through valves V7 and V8 to be used as a prewash.

Valves V19, V7, and V8 are closed after the washing step.

The centrifuge Z1 is now cleaned through valves V20, and V21 CIP (cleaning in place). This is necessary for removal of residues of the cell mass, since these would undergo lysis in the interval before the start of the next separation cycle. Following cleaning, valves V20 and V21 are closed and the centrifuge is steam sterilized through the main valves V7, V8, V10, and V22. The time at which sterilization is done is given in the batchwise process step described in Step 2. The separator is not used in this step.

The nutrient medium for the following process cycle is prepared in the vessel B1. First the medium components which can be sterilized by filtration are prepared and in analogy to Step 1.4 are manually transferred to fermenter F1 from vessel B1 through valve V11, sterilizing filter S1, and valve V2. At the same time medium which can be sterilized by filtration is transferred to the medium storage tanks S and A through the manually operated valves V12 and V13.

Subsequently, after being provided with process water through valve V17, vessel B1 is filled with medium components which cannot be sterilized by filtration and the concentrated solution is sterilized with heating mantle HM2 and indirectly cooled with water through HM2. During sterilization of vessel B1 the concentrated, filtration sterilized medium in F1 is diluted through sterilizing filter S1 and valve V2 with enough sterile process water so that after hot, heat-sterilized medium concentrate is dispensed from vessel B1 through valve V1 into fermenter F1, F1 is filled to the starting volume of the fermentation.

The process described below proceeds as described in Steps 2 through 6.

EXAMPLE 1

Implementation of a fermentation which is typical for the invention with Lactobacillus curvatus strain 2 DSM Number 4264. Implementation of the process can be subdivided into five steps which proceed cyclically after equipment start-up.

Step 1: Preparation and sterilization of the fermentation equipment and the nutrient medium components.

Before processing is started the fluid tightness of the equipment setup is tested and the preconditions for addition of media are satisfied by setting the appropriate valves. The fermenter equipment is then readied for operation. Nutrient media are weighted out and the tanks and vessels are filled. The equipment is sterilized.

Figure 9:
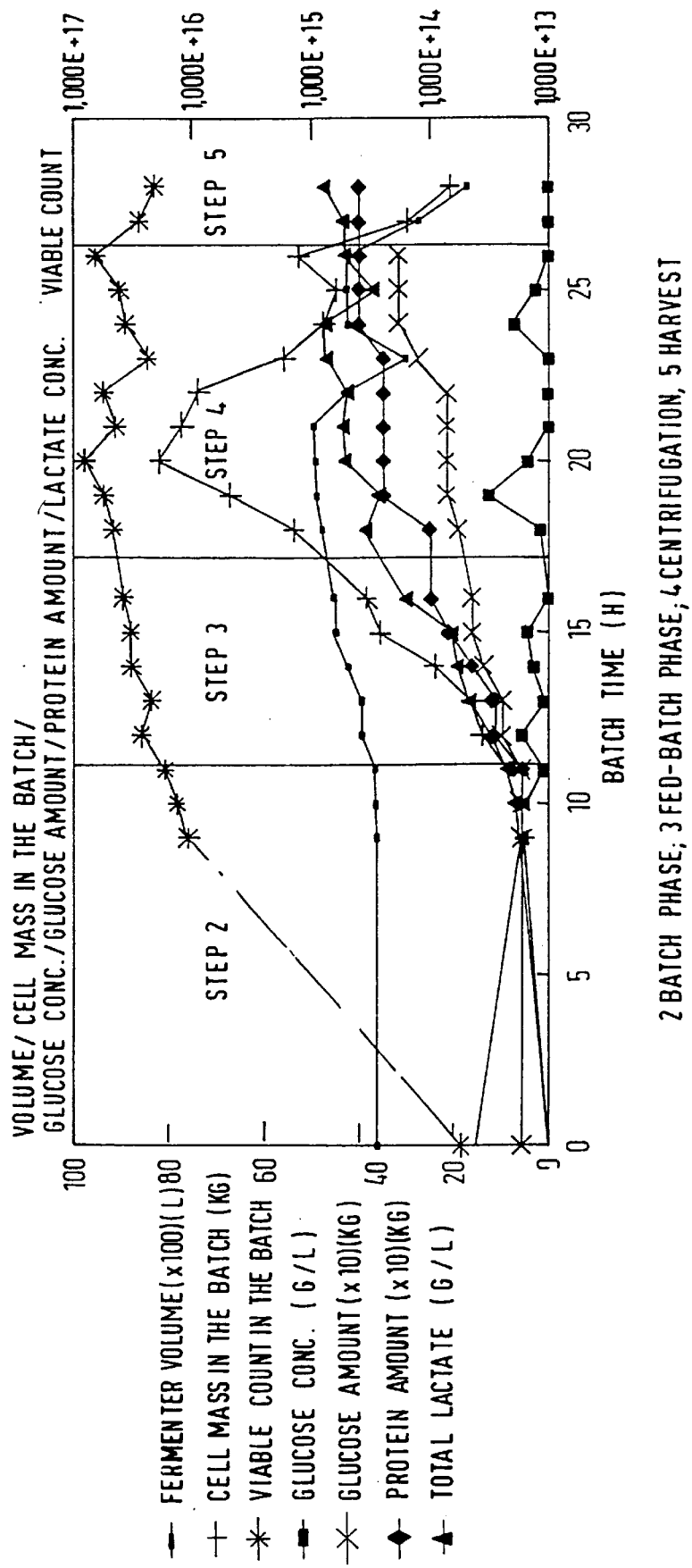
FIG. 9. Corresponds to FIG. 7 for *Lactobacillus curvatus* Strain 2.

FIGS. 9 and 10 show the course of the equipment- and process parameters.

Step 2: Start up of the fermentation by inoculation of the fermenter with starter culture, start up of the process control system and the first work cycle of the equipment as a batchwise procedure with low medium concentration and partial filling.

All working parameters are held constant during the course of the fermentation. The switch threshold to Step 3 is reached at the end of Step 2. The switch threshold is a defined glucose concentration of the medium. A defined amount of sodium hydroxide solution is used up until this switch threshold, set at approximately 1 gram per liter, is reached. When this amount of sodium hydroxide solution is used up, switching occurs.

Step 3: Transition to controlled medium dispensing until the final volume of the fermentation is reached.

Medium is dispensed under the control of the control substance, sodium hydroxide solution. In this example dispensing is done according to a stepwise function, which induces very rapid growth of the microorganism under consideration. (FIG. 10).

With other microorganisms constant dispensing is required for optimal growth. Any required dispensing function is available with the process control system.

Step 4: Transition to continuous procedure with exchange of nutrient medium and complete cell recycling or partial cell separation.

For the organism under consideration at the beginning of Step 4 under conditions of complete cell recycling the volume in the fermenter is reduced and thereafter medium is dispensed into the fermenter. As the process continues further cell recycling together with partial cell separation takes place. Subsequently, medium is again dispensed. The course of Step 4 described is typical for the organism under consideration. Different separation and dispensing intervals or constant dispensing and separation are used with other organisms (see FIG. 9).

Step 5: Termination of the continuous fermentation segment and harvest of the total biomass under sterile conditions.

Harvesting is started after the nutrient medium is completely exhausted, which is detected by termination of consumption of the sodium hydroxide solution. Harvesting is done without cell recycling, at the maximal separation efficiency of the centrifuge. The separation efficiency with the organism under consideration is poor compared to that with other organisms. The poor separation efficiency is due to the saccharide envelope of the organism, which hinders sedimentation. Organisms which lack saccharide envelopes enable the separator to achieve 2 to 3 times greater separation efficiency. Because of the poor sedimentation behavior of the organism due to the above-mentioned saccharide envelope, the organisms dealt with in the example make great demands on the progress of the process, since only relatively low medium exchange rates can be achieved.

Step 6: Readdition of sterile medium to the sterile equipment and repetition of the process according to Steps 1–5 with saving of total sterilization time and energy.

At the end of Step 4 the media tanks contain enough medium for readdition at the lower concentration. Directly following Step 5 sterile medium concentrate and sterile water are pumped into fermenter F1, which is immediately inoculated with another starter culture. Subsequently, during Step 2 of the process, media to be dispensed for the run in progress are prepared in the media storage tanks B1, S-storage tank and A-storage tank.

The processes are repeated with the allowing strains:

| Example 2: | Lactobacillus curvatus strain 3 | DSM 4265 |
| Example 3: | Pediococcus pentosaceus | DSM 6165 |
| Example 4: | Pediococcus acidilactici | DSM 6164 |
| Example 5: | Staphylococcus carnosus Sc1 | DSM 6162 |
| Example 6: | Micrococcus varians M28 | DSM 6163 |
| Example 7: | Micococcus varians M 101 | DSM 4263 |

The cultivation parameters are summarized in the following table.

| Culture Parameters of Starter Culture Strains | | | | | | | |
|---|---|---|---|---|---|---|---|
| Strain | LAB[1]) | LAC[2]) | PEB[3]) | PEC[4]) | SAB[5]) (ScA 1) | MIB[6]) (M 28) | MIC[7]) (M 101) |
| DSM Nr. | 4264 | 4265 | 6165 | 6164 | 6162 | 6163 | 4263 |
| Culture Temperature | 30° C. | 30° C. | 30° C. | 30° C. | 35° C. | 35° C. | 35° C. |
| Culture pH | 5.9 | 5.9 | 5.9 | 5.9 | 6.5 | 6.5 | 6.5 |
| Aeration %$O_2$ vvm | — | — | — | — | 20% $O_2$ | 20% $O_2$ | 20% $O_2$ |

-continued

Culture Parameters of Starter Culture Strains

| Strain | LAB[1]) | LAC[2]) | PEB[3]) | PEC[4]) | SAB[5]) (ScA 1) | MIB[6]) (M 28) | MIC[7]) (M 101) |
|---|---|---|---|---|---|---|---|
| DSM Nr. | 4264 | 4265 | 6165 | 6164 | 6162 | 6163 | 4263 |
| Gas Supply | $N_2$ | $N_2$ | $N_2$ | $N_2$ | pure $O_2$ | 0.14 vvm pure $O_2$ | 0.14 vvm pure $O_2$ |
| Stirrer Speed | 120 1/min | 120 1/min | 120 1/min | 120 1/min | 80–250 1/min | 80–250 1/min | 80–250 1/min |
| Inoculation Ratio | 1:562 | 1:562 | 1:1125 | 1:563 | 1:1000 | 1:80 | 1:80 |
| Total Culture Time | 24–26h | 24–26h | 24–26h | 24–30h | 14–17h | 18–20h | 18–20h |
| Alkali Consumption | 333 g NaOH /1000 g Glucose | 333 g NaOH /1000 g Glucose | 333 g NaOH /1000g Gluc. | 333 g NaOH /1000 g Glucose | 266 g NaOH /1000 g Glucose | 24 g NaOH /1000 g Glucose | 24 g NaOH /1000 g Glucose |
| Time of Harvest | Glucose exhaustion | Glucose exhaustion | Gluc. exhaustion | Glucose exhaustion | Glucose exhaustion | Glucose exhaustion | Glucose exhaustion |
| Separation Efficiency | 1400 1/h | 1400–1600 1/h | 2000–2400 1/h | 2000–2400 1/h | 3200 1/h | 3400 1/h | 3400 1/h |
| Working Volume of Fermenter | 4500 l | 4500 l | 4500 l | 4500 l | 4000 l | 4000 l | 4000 l |
| Switch Threshold from Step 2 (batch fermentation*) to Step 3 | 1 g/l Gluc. conc. in medium | 1 g/l Gluc. conc. in medium | 1 g/l Gluc. conc. in medium | 1 g/l Gluc. conc. in medium | 3 g/l Gluc. conc. in medium | Increase of $O_2$ partial pressure or increase of requirement for air | |

[1])*Lactobacillus curvatus* Strain 2
[2])*Lactobacillus curvatus* Strain 3
[3])*Pediococcus pentasaceus*
[4])*Pediococcus acidilactici*
[5])*Staphylococcus carnosus* Strain 1
[6])*Micrococcus varians* Strain M28
[7])*Mikrococcus varians* Strain M101

EXAMPLE 3

Implementation of a fermentation with the organism *Pediococcus pentosaceus*.

Implementation of the process according to the invention can be subdivided into five steps, which proceed cyclically after equipment start up.

Step 1: Preparation and sterilization of the fermenter equipment and the components of the nutrient medium.

Before processing is started the fluid tightness of the equipment is checked and the preconditions for addition of medium are satisfied by closing the appropriate valves. The fermentation equipment is then readied for operation. Nutrient media are weighed out and the tanks and vessels are filled. The equipment is sterilized.

Step 2: Start up of the fermentation by inoculation of the fermenter with the starter culture, start up of the process control system and the first work cycle of the equipment as a batchwise procedure with low medium concentration and partial filling.

Figure 7:
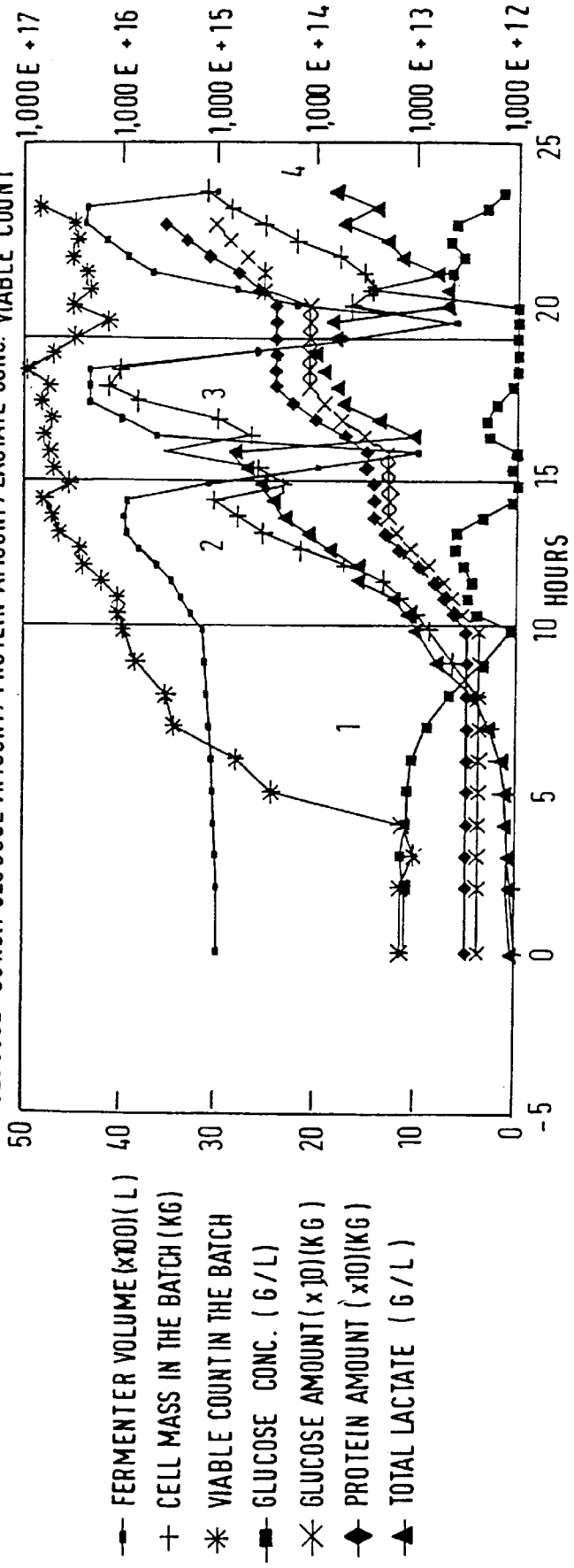
FIG. 7. Process parameters as a function of time in the cultivation of *Pediococcus pentosaceus;*
Figure 8:
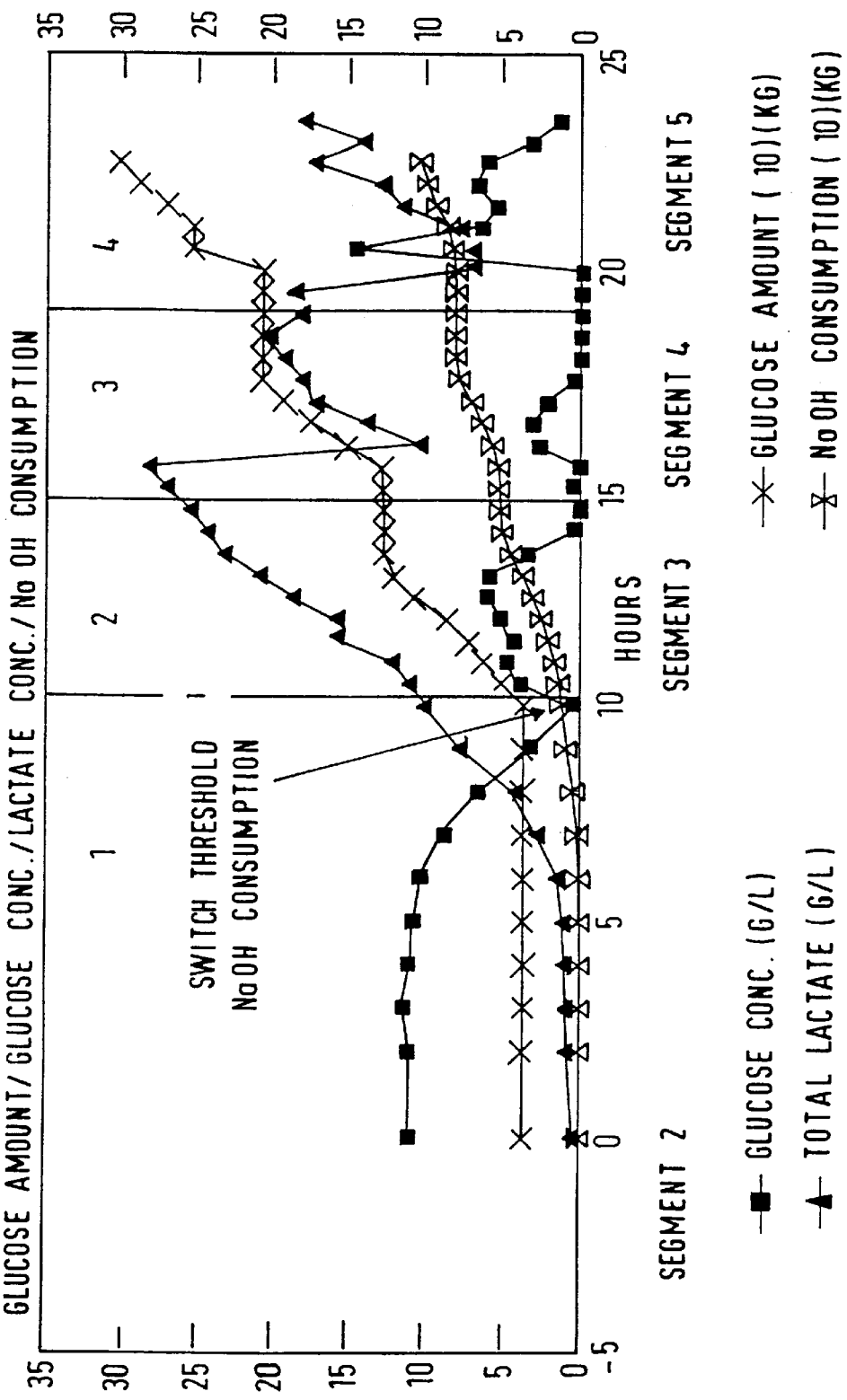
FIG. 8. Parameters selected from process parameters in the cultivation of *Pediococcus pentosacirus* show.

FIGS. 7 and 8, panel 1, batch phase, show the course of the equipment parameters. All operation parameters are held constant. At the end of Step 2 the switch threshold to Step 3 is reached. In this example the switch threshold is a defined glucose concentration of the medium. A defined amount of sodium hydroxide solution is consumed until this switch point, set at approximately 1 gram per liter, is reached. When this amount of sodium hydroxide solution is consumed, switching occurs. (see FIG. 8).

Step 3: Transition to controlled medium dispensing until the final volume of the fermenter is reached.

In this example medium is dispensed under the control of the control substance, sodium hydroxide solution. In this example medium is dispensed continuously, inducing very rapid growth. In FIG. 7 the continuous dispensing is shown by the increases in the fermenter volume and the quantities of glucose and protein. With other organisms a stepwise dispensing schedule is required to achieve optimal growth. Any dispensing function required is available with the process control system.

Step 4: Transition to continuous procedure with medium exchange and complete or partial cell recycling.

At the beginning of Step 4 the fermenter volume is reduced concomitantly with complete cell recycling; subsequently medium is dispensed. In continuation of the process there is further cell recycling together with partial cell separation. Medium is again dispensed. The described course of Step 4 is characteristic of the organism used. Different separation and dispensing intervals or continuous separation and dispensing are used with other organisms.

Step 5: Termination of the continuous fermentation segment and harvest of the total biomass under sterile conditions.

Harvesting is started after the nutrient medium is completely exhausted, which with this organism is detected by termination of consumption of the sodium hydroxide solution. Harvesting is done at the maximum separation efficiency of the centrifuge without cell recycling.

Step 6: Readdition of sterile nutrient medium to the sterile equipment and repetition of the process according to Steps 1–5 with saving of total sterilization time and energy.

At the end of Step 4 the media tanks contain enough medium for readdition at the lower concentration. Directly following Step 5 sterile medium concentrate and sterile water are pumped into fermenter F1 and immediately inoculated with another starter culture. Subsequently, during Step 2 of the process, media to be dispensed for the run in progress are prepared in the media storage tanks B1, S-storage tank and A-storage tank.

I claim:

1. Process for the production of cell mass under sterile conditions, comprising the following fermentation stages:
    a) a batch fermentation stage under sterile conditions comprising the steps of:
        1) charging a fermentor with a sufficient amount of nutrient medium concentrate to start a cell culture;
        2) sterilizing the fermentor and the nutrient medium concentrate therein and diluting the nutrient medium concentrate to a concentration sufficiently lower than a specific nutrient medium concentration to permit optimal cell multiplication and to establish adaptation of the cells to the nutrient medium;
        3) inoculating the nutrient medium with cells; and
        4) allowing undisturbed growth for a period of time prior to reaching conditions of substrate limitation;
    b) a fed-batch fermentation stage under sterile conditions comprising:
        adding nutrient medium to the dilute nutrient medium after said period of time to increase the concentration of the nutrient medium to said specific nutrient medium concentration to attain an exponential average growth rate of said cells, said adding of nutrient medium increasing the volume of the nutrient medium to a final volume of the fermentor to maintain said exponential average growth rate of said cells; and
    c) a continuous fermentation stage under sterilized conditions comprising the steps of:
        1) reducing the volume of the nutrient medium in the fermentor concomitantly with at least partial cell recycling and adding sterilized nutrient medium to the fermentor; and
        2) terminating the continuous fermentation stage by harvesting cells under sterile conditions after the nutrient medium is completely exhausted.

2. The process according to claim 1 wherein the amount of nutrient medium added in the continuous fermentation stage is increased proportionately to the exponential growth of the culture and is held constant when maximal cell separation is reached.

3. The process according to claim 1 wherein the nutrient medium is added under the control of a control parameter whose value is continuously determined, said control parameter being selected from the croup consisting of pH value, $CO_2$ value and $O_2$ concentration.

4. The process according to claim 3, wherein said pH value is determined in the fermentor and is held constant by addition of sodium hydroxide.

5. The process according to claim 4 wherein an amount of a sterilized nutrient medium is added which is equivalent to the amount of sodium hydroxide added, and which amount of nutrient medium varies in accordance with a factor k proportional to the growth rate of the cell culture during its growth phase.

6. The process according to claim 5 wherein nutrient medium becomes exhausted and is replaced according to a shell curve which is specific for the cell culture and which takes into account the cell mass present, the growth rate and the culture conditions of the cell culture.

7. The process according to claim 6 wherein the cell culture is adjusted to a required growth rate.

8. The process according to claim 1 wherein said undisturbed growth of the culture is implemented at least in part in batch mode.

9. The process according to claim 1 wherein the harvesting of the cells under sterile conditions further comprises separation of metabolites and the cells by centrifugation.

10. The process according to claim 1 wherein said diluting is carried out by injecting cold, sterile water.

11. The process according to claim 1 wherein during the harvesting of the cells under sterile conditions at least a portion of the cells is recycled.

12. The process according to claim 1 wherein said cells include aerobic cells and which process further includes the step of aerating the nutrient medium with air enriched with pure oxygen.

* * * * *

UNITED STATES PATENT AND TRADEMARK OFFICE
CERTIFICATE OF CORRECTION

PATENT NO.   : 5,981,260
DATED        : November 9, 1999
INVENTOR(S)  : Michael Metz It is certified that error appears in the above-identified patent and that said Letters Patent is hereby corrected as shown below:

Column 8 Line 43 "H1 and H1" should read --H1 and H2--.

Column 13 Line 46 "rate a" should read --rate $\mu$--.

Column 14 Line 37 "F1AMF1" should read --F1$\Delta$MF1--.

Column 17 Table-continued, 1st column, next-to-last row:
    after "batch fermentation" delete asterisk -- * --.

Column 19 Line 21, Claim 1(b), "comprising:" should read
    --comprising the step of:--.

Column 20 Line 7, Claim 3, "from the croup" should read
    --from the group--.

Column 20 Line 9, Claim 4, after "to claim 3" delete
    comma -- , --.

Signed and Sealed this

First Day of August, 2000

Attest:

Q. TODD DICKINSON

*Attesting Officer*          *Director of Patents and Trademarks*